US008435287B2

(12) United States Patent
Nakatani et al.

(10) Patent No.: US 8,435,287 B2
(45) Date of Patent: May 7, 2013

(54) STENT AND METHOD FOR FABRICATING THE SAME

(75) Inventors: Tatsuyuki Nakatani, Hiroshima (JP); Keishi Okamoto, Hiroshima (JP); Shuzo Yamashita, Okayama (JP); Ikuo Komura, Okayama (JP); Koji Mori, Okayama (JP)

(73) Assignees: Toyo Advanced Technologies Co., Ltd., Hiroshima-Shi (JP); Japan Stent Technology Co., Ltd, Okayama-shi (JP)

( * ) Notice: Subject to any disclaimer, the term of this patent is extended or adjusted under 35 U.S.C. 154(b) by 105 days.

(21) Appl. No.: 12/088,000

(22) PCT Filed: Jan. 15, 2007

(86) PCT No.: PCT/JP2007/050415
§ 371 (c)(1),
(2), (4) Date: Jul. 18, 2008

(87) PCT Pub. No.: WO2007/086269
PCT Pub. Date: Aug. 2, 2007

(65) Prior Publication Data
US 2011/0060403 A9  Mar. 10, 2011

Related U.S. Application Data

(63) Continuation-in-part of application No. 10/594,918, filed as application No. PCT/JP2005/005534 on Mar. 25, 2005, now abandoned.

(30) Foreign Application Priority Data

Jan. 30, 2006  (JP) ................... 2006-020926

(51) Int. Cl.
*A61F 2/06* (2006.01)
(52) U.S. Cl.
USPC ................... 623/1.42; 623/1.44; 623/1.46
(58) Field of Classification Search ........... 623/1.11, 623/1.13, 1.44, 1.46, 1.42, 1.49
See application file for complete search history.

(56) References Cited

U.S. PATENT DOCUMENTS

| 5,725,573 | A  | * | 3/1998 | Dearnaley et al. | 427/2.25 |
|---|---|---|---|---|---|
| 5,735,896 | A  | * | 4/1998 | Amon et al. | 424/423 |
| 6,562,445 | B2 | * | 5/2003 | Iwamura | 428/217 |
| 6,572,651 | B1 | * | 6/2003 | De Scheerder et al. | 623/1.44 |
| 6,761,736 | B1 | * | 7/2004 | Woo et al. | 623/2.42 |
| 7,931,934 | B2 | * | 4/2011 | Nakatani et al. | 427/2.25 |
| 2003/0104028 | A1 | * | 6/2003 | Hossainy et al. | 424/424 |

(Continued)

FOREIGN PATENT DOCUMENTS

| CA | 2561667 A1 | * | 3/2005 |
|---|---|---|---|
| JP | 10-248923 A |   | 9/1998 |

(Continued)

*Primary Examiner* — Thomas J Sweet
*Assistant Examiner* — Seema Mathew
(74) *Attorney, Agent, or Firm* — Birch, Stewart, Kolasch & Birch, LLP

(57) ABSTRACT

A stent includes a tubular stent body 11, a diamond-like carbon film 12 formed on the surface of the stent body 11 and having an activated surface, and a polymer layer 13 immobilized on the surface of the diamond-like carbon film. The polymer layer 13 contains a drug 14 having an effect to prevent restenosis, and the drug 14 is gradually released from the polymer layer 13.

14 Claims, 2 Drawing Sheets

U.S. PATENT DOCUMENTS

| | | | |
|---|---|---|---|
| 2003/0191354 A1* | 10/2003 | Grabowy | 600/3 |
| 2007/0207321 A1* | 9/2007 | Abe et al. | 428/413 |
| 2008/0286588 A1* | 11/2008 | Burgess et al. | 428/469 |
| 2009/0005862 A1 | 1/2009 | Nakatani et al. | 623/1.49 |
| 2009/0246243 A1* | 10/2009 | Martinu et al. | 424/423 |
| 2010/0136212 A1* | 6/2010 | Abe et al. | 427/2.25 |
| 2010/0247917 A1* | 9/2010 | Nitta et al. | 428/408 |
| 2011/0195580 A1* | 8/2011 | Okada et al. | 438/763 |

FOREIGN PATENT DOCUMENTS

| | | |
|---|---|---|
| JP | 2001-029447 A | 2/2001 |
| JP | 2002-517285 A | 6/2002 |
| JP | 2003-033439 A | 2/2003 |
| JP | 2005-168937 A | 6/2005 |
| JP | 2005-170801 A | 6/2005 |
| JP | 2005-531332 A | 10/2005 |
| WO | WO-99/64085 A1 | 12/1999 |
| WO | WO-02/080996 A1 | 10/2002 |
| WO | WO-03/020329 A1 | 3/2003 |
| WO | WO 03/086496 A1 | 10/2003 |
| WO | WO-2004/108129 A1 | 12/2004 |
| WO | WO-2005/097673 A1 | 10/2005 |

\* cited by examiner

STENT AND METHOD FOR FABRICATING THE SAME

This application is a National Stage application of PCT International Application No. PCT/JP2007/050415 filed on Jan. 15, 2007 which designated the United States, and is a Continuation-in-Part of co-pending application Ser. No. 10/594,918 filed on Sep. 29, 2006 and for which priority is claimed under 35 U.S.C. §120. Application Ser. No. 10/594,918 is a National Stage of PCT International Application No. PCT/JP05/005534 filed on Mar. 25, 2005 under 35 USC §371.

TECHNICAL FIELD

The present invention relates to a stent and a method for fabricating the same, and more particularly, it relates to a drug release stent and a method for fabricating the same.

BACKGROUND ART

In accordance with recent westernization in the lifestyle, ischemic heart diseases (including angina pectoris and cardiac infarction) are rapidly increasing in Japan. An ischemic heart disease is caused principally when coronary thrombosis or coronary twitch is caused additionally to an arteriosclerotic disease of a thick coronary artery extending on the heart surface.

As a treatment method for angiostenosis, angioplasty (PTA, PTCA or the like) in which a small balloon is expanded within a blood vessel for the treatment is widely employed as a minimally invasive treatment. In employing this treatment method, however, stenosis (restenosis) is repeatedly caused in high probability. As a method for reducing the ratio of the restenosis, a stent placement technique is being rapidly spreading these days.

Since a stent is used to be indwelled in a body, it is required to have durability against biological materials and compatibility with an organism. As a method for providing a medical material such as a stent with durability, a method in which the surface of the medical material is coated with a diamond-like carbon film (a DLC film) is known (see, for example, Patent Document 1). Since a DLC film is a very smooth and chemically inert film, it is characterized by being minimally reactive with biogenic components. Accordingly, when the surface of a base material of a stent is coated with a DLC film, a stent with high durability and good biocompatibility can be obtained.

On the other hand, it has been reported that the restenosis occurs at frequency of approximately 20% through 30% also in employing the stent indwelling technique. In the case where the restenosis occurs, it is necessary to perform the PTCA again, and it is a global problem of great urgency to establish methods for preventing and treating the restenosis.

As a method for preventing the restenosis, an attempt has been made to coat the base material of a stent with a drug for restricting the occurrence of occlusion. For example, Patent Document 2 discloses a method for coating a stent by spraying a polymer solution including a drug over the surface of the stent or by immersing the stent in the polymer solution. Thus, a stent from which an anti-restenosis drug is gradually released can be realized.

Patent Document 1: Japanese Laid-Open Patent Publication No. 10-248923

Patent Document 2: National Publication of Translated Version No. 2005-531332

Patent Document 3: National Publication of Translated Version No. 2002-517285

DISCLOSURE OF THE INVENTION

Problems to be Solved by the Invention

However, a conventional stent has a problem that it is difficult to continuously release the drug because the coated polymer is peeled off. Since a stent is largely physically deformed in use, when the base material is physically coated with the polymer by, for example, spraying the polymer solution over the surface of the base material, cracks are caused so that the polymer can be easily peeled off.

In particular, in the case where the surface of the base material is covered with a DLC film, since the surface of the DLC film is inert and smooth, the physical interaction between the polymer and the DLC film is so small that the polymer is more easily peeled off. Therefore, the anti-restenosis drug cannot be continuously released from the stent, and hence, the restenosis cannot be effectively prevented.

On the other hand, a method in which biogenic molecules are chemically immobilized on the surface of a DLC film by using a linker molecule is known (see, for example, Patent Document 3), but it is difficult in this case to gradually release the biogenic molecules. Also, since it is necessary to use a linker molecule, there are problems that it is complicated to immobilize the biogenic molecules and that the kinds of biogenic molecules to be immobilized are limited.

An object of the present invention is solving the aforementioned conventional problems for realizing a stent including a base material not degraded by a biogenic component and capable of continuously releasing a drug for preventing the restenosis.

Means for Solving Problems

In order to achieve the object, in the stent of this invention, a drug release polymer is immobilized on the surface of a DLC film with a functional group introduced into a surface portion of the DLC film.

Specifically, the stent of this invention includes a tubular stent body; a diamond-like carbon film formed on a surface of the stent body and having an activated surface; and a polymer that is immobilized on the surface of the diamond-like carbon film, contains an anti-restenosis drug and gradually releases the drug.

Since the stent of this invention includes the diamond-like carbon film formed on the surface of the stent body and having the activated surface, a base material of the stent is minimally degraded. Also, since the polymer can be tightly immobilized, even when the stent is largely deformed in use, the polymer gradually releasing the drug is never peeled off from the surface of the stent. Accordingly, the drug can be continuously released from the stent, and hence the restenosis is minimally caused.

In the stent of this invention, the diamond-like carbon film preferably has a thickness not less than 10 nm and not more than 300 nm. Thus, the diamond-like carbon film can be prevented from peeling off from the stent body, so that the stent can be used for a long period of time.

The stent of this invention preferably further includes an intermediate layer formed between the stent body and the diamond-like carbon film, and the intermediate layer is preferably made of an amorphous film including at least one of silicon and carbon as a principal component. Thus, the adhesiveness between the diamond-like carbon film and the stent is improved, so as to definitely prevent the degradation of the base material.

In this case, the intermediate layer preferably has a thickness not less than 5 nm and not more than 100 nm.

In the stent of this invention, the stent body is preferably made of one of a metal material, a ceramic material and a polymeric material, or preferably is a complex made of at least two of a metal material, a ceramic material and a polymeric material.

In the stent of this invention, a surface portion of the diamond-like carbon film preferably has a hydrophilic functional group. Thus, the biocompatibility of the surface of the diamond-like carbon film can be improved.

In the stent of this invention, the polymer is preferably immobilized on the surface of the diamond-like carbon film through ionic interaction. Thus, the polymer can be definitely prevented from peeling off from the surface of the diamond-like carbon film.

In the stent of this invention, the polymer is preferably a biocompatible polymer.

In this case, the biocompatible polymer is preferably at least one polymer or an ester of a polymer selected from the group consisting of polyurethane, polyacrylamide, polyethylene oxide, polyethylene carbonate, polyethylene, polyethylene glycol, polypropylene carbonate, polyamide, fibrin, a polymer of phospholipid, a hydrophobic/hydrophilic microphase-separated polymer, a polymer or a copolymer of hydroxyethyl methacrylate, a polymer or a copolymer of vinyl pyrrolidone, a polymer or a copolymer of a fluorine-containing monomer, a polymer or a copolymer of a Si-containing monomer, and a polymer or a copolymer of vinyl ether.

In the stent of this invention, the polymer is preferably a biodegradable polymer.

In this case, the biodegradable polymer is preferably at least one polymer selected from the group consisting of polylactic acid, polyglycolic acid, a copolymer of polylactic acid and polyglycolic acid, collagen, gelatin, chitin, chitosan, hyaluronic acid, polyamino acid, starch, poly-ε-caprolactone, polyethylene succinate and poly-β-hydroxylalkanoate.

In this case, the biodegradable polymer preferably includes a plasticizing agent. Thus, the decomposition of the biodegradable polymer in vivo is accelerated, so as to improve the efficiency in releasing the drug.

In the stent of this invention, the drug is preferably at least one drug selected from the group consisting of an antiplatelet drug, an anticoagulant, an antifibrin, an antithrombin, an anti-proliferative agent, an anticancer agent, an inhibitor of HMG-CoA reductase, alfa-interferon and genetically modified epithelial cells.

The method for fabricating a stent of this invention includes a diamond-like carbon film forming step of forming a diamond-like carbon film on a surface of a stent body; a surface activation step of producing reactive sites in a surface portion of the diamond-like carbon film; and a polymer layer forming step of immobilizing a polymer containing a drug onto a surface of the diamond-like carbon film after the surface activation step.

Since the method for fabricating a stent of this invention includes the activation step of producing the reactive sites in the surface portion of the diamond-like carbon film, the degradation of the stent body is prevented as well as the polymer containing the drug can be tightly immobilized on the surface of the diamond-like carbon film. Accordingly, even when the stent is largely deformed in use, the polymer can be prevented from peeling off. As a result, a stent minimally degraded in its base material and capable of continuously releasing the drug can be realized.

The method for fabricating a stent of this invention preferably further includes, before the diamond-like carbon film forming step, an intermediate layer forming step of forming an amorphous film including silicon and carbon as principal components on the surface of the stent body. Thus, the adhesiveness between the diamond-like carbon film and the stent body can be improved.

In the method for fabricating a stent of this invention, the surface activation step is preferably plasma irradiation step of irradiating the surface of the diamond-like carbon film with plasma. In this case, the plasma is preferably plasma of one gas or a mixed gas of two or more gases selected from the group consisting of argon, xenon, neon, helium, krypton, nitrogen, oxygen, ammonia, hydrogen, steam, chain or cyclic hydrocarbon, an organic compound including oxygen and an organic compound including nitrogen. Thus, a functional group can be definitely introduced into the surface portion of the diamond-like carbon film.

The method for fabricating a stent of this invention preferably further includes, between the surface activation step and the polymer layer forming step, a surface treatment step of introducing hydroxyl groups onto the surface portion of the diamond-like carbon film by reacting between the reactive sites and molecules including oxygen.

In the method for fabricating a stent of this invention, the polymer is preferably a biocompatible polymer or a biodegradable polymer.

Effect of the Invention

According to the present invention, a stent including a base material not degraded by a biogenic component and capable of continuously releasing a drug for preventing restenosis can be realized.

BRIEF DESCRIPTION OF DRAWINGS

FIG. 1A is a perspective view of the whole stent and FIG. 1B is a cross-sectional view thereof taken on line Ib-Ib of FIG. 1A.

DESCRIPTION OF REFERENCE NUMERALS 10 stent
11 stent body
12 diamond-like carbon film
13 polymer layer
14 drug
21 plasma generator
22 material
31 chamber
32 vacuum pump
33 electrode
34 electrode
35 radiofrequency power supply
36 matching network Best Mode for Carrying Out the Invention A stent according to an embodiment of the invention will now be described with reference to the accompanying drawings. FIGS. 1A and 1B show the stent of this embodiment, and FIG. 1A shows the schematic shape of the stent and FIG. 1B shows the cross-sectional structure thereof taken on line Ib-Ib of FIG. 1A.

As shown in FIGS. 1A and 1B, the stent 10 of this embodiment includes a diamond-like carbon film (DLC film) 12 formed on the surface of a stent body 11 made of a metal or the like. The surface of the DLC film 12 has been subjected to activation. The activation is performed by plasma irradiation, ultraviolet (UV) irradiation, ozonization or the like as described later.

Figure 1A:
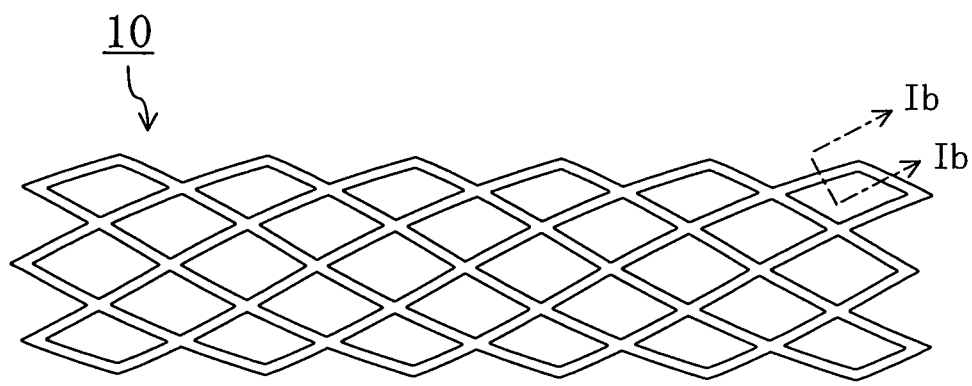
FIGS. 1A and 1B are diagrams of a stent according to an embodiment of the invention.
Figure 1B:
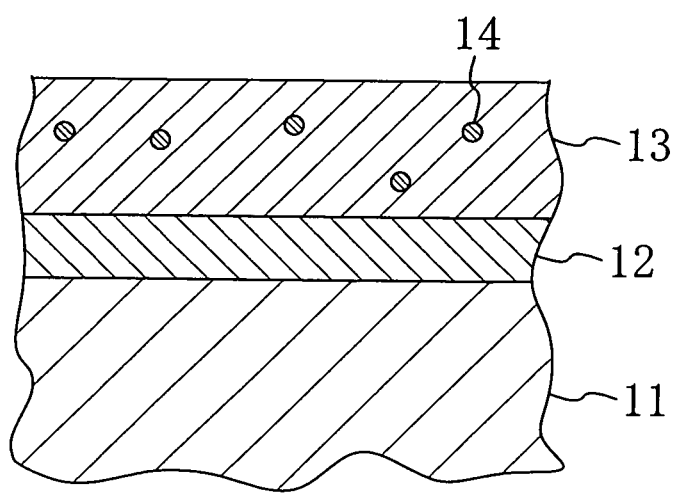

The surface of the DLC film 12 having been subjected to the activation is coated with a polymer layer 13. Since the surface of the DLC film 12 has been subjected to the activation, the polymer layer 13 is tightly immobilized onto the surface of the DLC film 12. The polymer layer 13 contains a drug 14 for prevention of restenosis, and the drug 14 is gradually released from the polymer layer 13. Thus, a stent capable of continuously releasing the drug for a long period of time can be realized.

Now, the respective components of the stent will be described in detail.

—Stent Body—

The stent body 11 is not particularly specified and may be made of any of generally known materials. For example, it is obtained by cutting with laser, into a stent design, a metal tube made of stainless steel, a nickel titanium (Ni—Ti) alloy, a copper aluminum manganese (Cu—Al—Mn) alloy, tantalum, a cobalt chromium (Co—Cr) alloy, iridium, iridium oxide, niobium or the like and electrolytic polishing the resultant. Alternatively, it may be obtained by a method in which a metal tube is etched, a method in which a metal plate is cut with laser to be rolled into a cylinder and welded, a method in which a metal wire is knit, or the like.

Also, the material for the stent body 11 is not limited to the metal material, but a polymeric material such as polyorefin, polyorefin elastomer, polyamide, polyamide elastomer, polyurethane, polyurethane elastomer, polyester, polyester elastomer, polyimide, polyamide-imide or polyether ether ketone, or an inorganic material such as ceramics or hydroxyapatite may be used. A method for processing such a polymeric or inorganic material into a stent does not affect the effects of the invention, and a processing method appropriate for each material may be arbitrarily selected.

—Formation of Diamond-Like Carbon Film—

The diamond-like carbon film (DLC film) 12 is a thin film of carbon similar to diamond and is so dense and digit that biogenic components cannot permeate through the DLC film 12. Therefore, when the surface of the stent body 11 is covered with the DLC film 12, the degradation of the stent body 11 otherwise caused by biogenic components can be prevented.

Furthermore, there are micro-scale or nano-scale irregularities on the material surface of the stent body 11. These irregularities can be a starting point of adhesion of a biogenic component, and the adhesion of a biogenic component onto the stent body 11 may cause thrombus or the like. However, when the stent body 11 is covered with the DLC film 12, the irregularities are smoothed. The stent body 11 covered with the smooth and inert DLC film 12 is minimally interacted with a biogenic component so that the adhesion of the biogenic component onto the stent can be reduced.

In this embodiment, the DLC film 12 can be formed on the stent body 11 by any of known methods such as sputtering, DC magnetron sputtering, RF magnetron sputtering, chemical vapor deposition (CVD), plasma CVD, plasma ion implantation, superposed RF plasma ion implantation, ion plating, arc ion plating, ion beam evaporation or laser abrasion.

The thickness of the DLC film 12 is preferably large from the viewpoint of preventing the degradation of the stent body 11 by a biogenic component. However, since the stent is largely deformed in use, if the thickness of the DLC film 12 is too large, a crack may be caused in the deformation, which leads to a problem of peeling of the DLC film. Accordingly, the thickness of the DLC film 12 is not less than 10 nm and not more than 30 nm and is preferably not less than 20 nm and not more than 80 nm.

Although the DLC film may be directly formed on the surface of the stent body 11, an intermediate layer may be provided between the stent body 11 and the DLC film 12 for more tightly adhering the DLC film 12 onto the stent body 11.

The intermediate layer can be made of any of various materials in accordance with the material of the stent body 11 and may be made of a known material such as an amorphous film of silicon (Si) and carbon (C), titanium (Ti) and carbon (C) or chromium (Cr) and carbon (C).

Since the intermediate layer should be uniformly formed on the stent body 11, it needs to have a given thickness. When the thickness is too large, however, it takes a long time to form it, which lowers the productivity. Accordingly, the thickness of the intermediate layer is not less than 5 nm and not more than 100 nm and is preferably not less than 10 nm and not more than 40 nm.

The intermediate layer may be formed by any of known methods, such as the sputtering, the CVD, the plasma CVD, spray coating, the ion plating or the arc ion plating.

—Activation of Diamond-Like Carbon Film—

Since the surface of the DLC film 12 is smooth and inert as described above, when the surface of the DLC film 12 is directly coated with a polymer, the polymer is peeled off soon.

On the other hand, when the surface of the DLC film 12 is irradiated with plasma or the like, part of diamond (carbon-carbon) bonds formed on the surface can be cleaved. Thus, free radicals or ion seeds can be produced in a surface portion of the DLC film 12. When the free radicals or ion seeds are used, easily reactive functional groups such as carboxyl groups or hydroxyl groups can be easily introduced into the surface portion of the DLC film 12, and these functional groups can be replaced with another functional groups.

When the surface of the DLC film 12 is activated through the introduction of the functional groups, the surface of the DLC film 12 can be tightly coated with any of various polymers.

The carbon-carbon bonds of the DLC film 12 may be cleaved by exposing the DLC film to plasma generated from a gas of, for example, argon (Ar), neon (Ne), helium (He), krypton (Kr), xenon (Xe), nitrogen ($N_2$), oxygen ($O_2$), ammonia ($NH_4$), hydrogen ($H_2$) or steam ($H_2O$). One of such gases may be singly used or a mixture thereof may be used. Alternatively, the carbon-carbon bonds may be cleaved through irradiation with ultraviolet or irradiation with ultraviolet in an ozone atmosphere.

Since a cleaved carbon-carbon bond is easily reacted with water, a hydroxyl group or a carboxyl group can be easily introduced into the surface portion of the DLC film 12. Also, a hydroxyl group or a carboxyl group once introduced can be easily replaced with another functional group. For example, a hydroxyl group introduced into the surface portion of the DLC film 12 can be easily replaced with an amino group, a carboxyl group, an isocyanate group or a vinyl group through a reaction with a functional alkoxysilane derivative such as 3-aminopropyl trimethoxysilane, a functional carboxylic acid derivative such as 2-mercaptoacetic acid, a diisocyanate derivative, 2-methacryloyloxy ethyl isocyanate, 2-acryloyloxy ethyl isocyanate, N-methacryloyl succinimide, N-acryloyl succinimide or the like.

When hydroxyl groups or carboxyl groups are introduced into the surface portion of the DLC film 12, the hydrophilic property of the surface of the DLC film 12 is improved. Thus, the biocompatibility of the DLC film 12 itself is preferably improved. In this case, even when the groups are replaced with another functional groups, a part of hydroxyl groups or carboxyl groups are not replaced but remain, and therefore, the effect to improve the biocompatibility of the DLC film 12 itself can be retained.

In the case where chain or cyclic hydrocarbon, an organic compound including oxygen or an organic compound including nitrogen is used as the gas corresponding to the plasma source, the carbon-carbon bonds are not only cleaved but also reacted with ion seeds included in the plasma, and functional groups in accordance with the gas seed can be directly introduced into the surface portion of the DLC film 12.

The kind of functional groups to be introduced into the surface portion of the DLC film 12 is appropriately selected in accordance with the kind of polymer used for the polymer layer 13 to be immobilized onto the DLC film 12. For example, when the functional group to be introduced into the surface portion of the DLC film 12 is an ionic functional group such as a carboxyl group, an amino group or a phosphoric acid group, a polymer can be immobilized onto the surface of the DLC film 12 through ionic interaction (ion bonding) by using an ionic functional group included in the polymer.

Alternatively, when a hydrophobic functional group is introduced, a polymer can be physically immobilized by increasing the physical interaction with the polymer.

Furthermore, in the case where a polymer includes, in its molecule, a functional group of an isocyanate group or a trialkyl oxysilane group such as trimethoxysilane or trimethoxysilane, when a functional group to be introduced into the surface portion of the DLC film 12 is an amino group, the functional groups can be covalent bonded with each other. Alternatively, a bifunctional reagent may be used for bonding a functional group introduced into the surface portion of the DLC film 12 and a functional group included in a polymer, and in this case, the kind of functional group to be introduced into the surface portion of the DLC film 12 is selected in accordance with the kind of bifunctional reagent.

—Polymer Layer—

The polymer layer 13 is formed by immobilizing a polymer onto the surface of the DLC film 12. The polymer to be immobilized on the surface of the DLC film 12 is preferably a polymer that is immobilizable onto the activated DLC film 12, contains a drug therein and is capable of releasing the drug at a given speed. Furthermore, a polymer onto which a blood platelet is minimally adhered and which is not stimulative against a tissue is preferred.

Examples of the polymer are biodegradable polymers such as polyglycolic acid, a copolymer of lactic acid and glycolic acid, poly(DL-lactic acid) (DL-PLA), poly(L-lactic acid) (L-PLA), lactide, polycaprolactone (PCL), collagen, gelatin, chitin, chitosan, hyaluronic acid, polyamino acid such as poly(L-glutamic acid) or poly-L-lysine, poly-ε-caprolactone, polyethylene succinate and poly-β-hydroxyalkanoate. Furthermore, a polar functional group may be introduced into the terminal of polylactic acid, polyglycolic acid or a copolymer of polylactic acid and polyglycolic acid.

In addition, any biodegradable polymer can be used as far as it is enzymatically or nonenzymatically decomposed in vivo, a decomposition product thereof does not exhibit toxicity and it is capable of releasing a drug.

Furthermore, a plasticizing agent may be added for accelerating the decomposition in vivo and for efficiently releasing the drug. As the plasticizing agent, for example, a plasticizing ester of tartaric acid, malic acid or citric acid, or another plasticizing agent having been confirmed in the safety against organism may be used.

Alternatively, a non-decomposable polymer with biocompatibility may be used. For example, parylene, Parylast®, polyethylene, polyethylene terephthalate, ethylene vinyl acetate, silicon, polyethylene oxide (PEO), polybutyl methyl acrylate, polyacrylamide, polycarbonate such as polyethylene carbonate or polypropylene carbonate, polyurethane such as segmented polyurethane, or a synthetic polymer such as a blend or a block copolymer of polyether type polyurethane and dimethyl silicon may be used. Alternatively, a natural polymer such as fibrin may be used.

It is noted that a functional group or the like may be introduced if necessary for immobilizing the polymer onto the DLC film.

—Drug—

The drug to be contained in the polymeric material may be any drug as far as it exhibits the anti-restenosis effect. For example, an antiplatelet drug, an anticoagulant, an antifibrin, an antithrombin, a thrombolytic drug, an antiproliferative agent, an anticancer agent, an immunosuppressive agent, an antibiotic, an anti-inflammatory drug or the like can be used. Specific examples of the drug will now be described, which are merely illustratively mentioned and do not limit the invention.

Examples of the antiplatelet drug, the anticoagulant, the antifibrin and the antithrombin are heparin sodium, low molecular weight heparin, hirudin, argatroban, forskolin, sarpogrelate hydrochloride, vapiprost, prostacyclin, prostacyclin homologues, dextran, D-phe-pro-arg-chloromethylketone (synthetic antithrombin), dypyridamole, a glycoprotein IIb/IIIa platelet membrane receptor antibody, a vitronectin receptor antagonist and thrombin inhibitors.

Examples of the thrombolytic drug are a tissue plasminogen activator, streptokinase and urokinase.

Examples of the antiproliferative agent are angiotensin converting enzyme inhibitors such as angiopeptin, captopril, cilazapril and lisinopril, a calcium channel blocker antibody, colchicine, a fibroblast growth factor (FGF) antagonist, fish oil (omega 3-fatty acid), a histamine antagonist, lovastatin (an inhibitor of HMG-CoA reductase), methotrexate, nitroprusside, a phosphodiesterase inhibitor, a prostaglandin inhibitor, seramin (a PDGF antagonist), a serotonin blocker antibody, steroid, a thioprotease inhibitor, triazolopyrimidine (a PDGF antagonist), nitrogen oxide, all-trans retinoic acid, 13-cisretinoic acid and 9-cisretinoic acid (alitretinoin).

Alternatively, any of antiproliferative antimitotic alkylating drugs such as nitrogen mustards (including mechlorethamine, cyclophosphamide and an analogue thereof, melphalan, chlorambucil and the like), ethyleneimine, methylmelamine (including hexamethylmalamine, thiotepa and the like), a sulfonic acid alkyl-busulfan complex, nitrosoureas (including carmustine (BCNU), a BCNU analogue, sutreptozocin and the like) and a trazenes-dacarbazine (DTIC) complex may be used.

Alternatively, any of pyrimidine analogues (such as fluorouracil, floxuridine and cytarabine), purine analogues (such as mercaptopurine, thioguanine, pentostatin and 2-chlorodeoxyadenosine) and other inhibitors may be used. Any of antiproliferative antimitotic metabolic antagonists such as platinum coordination complexes (such as cisplatinum and carboplatin), procarbazine, hydroxyurea, mitotane, aminoglutethimide and hormones (including estrogen and the like) may be used. An enzyme such as L-asparaginase that systemically metabolizes L-asparagine for depriving various cells not having a function to autogenously synthesize asparagine may be used.

Examples of the anticancer agent are alkaloids such as taxol, taxotere and Topotecin, antibiotics such as Adriacin and Bleo, metabolic antagonists such as 5-FU and natural products such as vinca alkaloids (such as vinblastine, vincristine and vinorelbine).

Examples of the immunosuppressive agent are cyclospolin, tacrolimus (FK-506), sirolimus (rapamycin), azathioprine and mycophenolate mofetil. Examples of the antibiotic are dactinomycin (actynomycin D), daunorubicin, doxorubicin, idarubicin, anthracycline, mitozantrone, bleomycin, plicamycin (mithramycin) and mitomycin.

Examples of the anti-inflammatory drug are aspirin, dipyridamole, ticlopidine, clopidogrel, abciximab, antimigratory, an antisecretory agent (breveldin), adrenocortical steroids (such as cortisol, cortisone, fludrocortisone, prednisone, prednisolone, 6α-methylprednisolone, triamcinolone, betamethasone and dexamethazone), non-steroidal drugs (such as a salicylic acid derivative, namely, aspirin, and a paraaminophenol derivative, namely, acetaminophen), indole acetic acid and indene acetic acid (such as imdomethacin, sulindac and etodalac), heteroarylacetic acid (such as tolmetin, diclofenac and ketorolac), arylpropionic acid (such as ibuprofen and a derivative thereof), anthranilic acid (such as mefenamate and meclofenamate), enolic acid (such as piroxicam, tenoxicam, phenylbutazone and oxyphenthatrazone), nabumetone and gold compounds (such as auranofin, gold thioglucose and sodium aurothiomalate).

Alternatively, alfa-interferon, an angiogenic agent, a vascular endothelical growth factor (VEGF), an angiotensin receptor blocking agent, a nitrogen oxide donor, antisense oligonucleotides and a combination of them, a cell cycle inhibitor, a mTOR inhibitor, a growth factor signal transduction kinase inhibitor, retenoid, a cyclin/CDK inhibitor, an HMG coenzyme reductase inhibitor (statins), a protease inhibitor or the like can be used.

Furthermore, one of the aforementioned drugs may be singly used or a plurality of them may be used together. Moreover, instead of the drug, epithelial cells having genes engineered for discharging various drugs by the gene engineering technique may be used.

The drug having the effect to prevent the restenosis may be held in the polymer by any of known methods. For example, the drug can be held in the polymer by mixing the polymer in the form of a gel and the drug in a given concentration. In this case, the drug is held in the polymer through the physical interaction or the ionic interaction. Alternatively, depending upon the kind of polymer to be used, the drug may be subsumed by the three-dimensional structure of the polymer. When a solution or the like obtained by mixing the polymer and the drug is used for immobilizing the polymer onto the DLC film, the drug can be held in the polymer at the same time as the polymer is immobilized onto the DLC film.

—Immobilization of Polymer—

The polymer is immobilized onto the surface of the DLC film 12 by immersing, in a polymer solution, the stent body 11 having the activated DLC film 12 or by spraying or dropping a polymer solution over the stent body 11 having the activated DLC film 12. When the immersion is employed in particular, the polymer can be efficiently immobilized on the stent because the inner surface easily comes into contact with the polymer solution.

As a solvent of the polymer solution used in the dipping or spraying, an arbitrary solvent with solubility in the polymer can be selected. A mixed solvent including two or more solvents can be used in order to adjust the volatility of the solvent. Alternatively, it is not necessary to dissolve the polymer in the solvent but the solution may be a suspension or dispersion. Furthermore, when a liquid polymer is used, the polymer can be used as it is without using a solvent. Alternatively, the polymer may be placed in a melted state for use.

The concentration of the polymer solution is not particularly specified and is determined in consideration of the surface characteristic of the polymer layer 13, the necessary amount of drug to be held, the releasing behavior of the held drug and the like.

The ultimate thickness of the polymer layer 13 needs to be large from the viewpoint of the thickness uniformity of the polymer layer 13 on the stent surface, but if it is too large, a crack may be caused during the use of the stent. Therefore, the thickness is not less than 0.1 µm and not more than 200 µm and is preferably not less than 1 µm and not more than 100 µm.

Alternatively, the polymer layer 13 may include a plurality of layers. In this case, the drug may be contained in merely some of the layers. Alternatively, the respective layers may include different kinds of polymers. For example, an undercoat layer in contact with the DLC film may include a polymer with high adhesiveness to the DLC film, and a topcoat layer in contact with blood may include a biocompatible material such as silicon resin or a biodegradable polymer such as polylactic acid. Instead, a polymer including an antithrombotic material such as heparin may be used. In this case, a polymer included in the topcoat layer may be selected in consideration of an esthetic effect such as a color and luster.

EXAMPLE

The stent of the present invention will now be described in detail by describing a specific example. In this example, a Co—Cr alloy stent having a length of 19 mm, a diameter of 1.5 mm and a cell thickness of 75 µm was used as the stent body 11.

Figure 2:
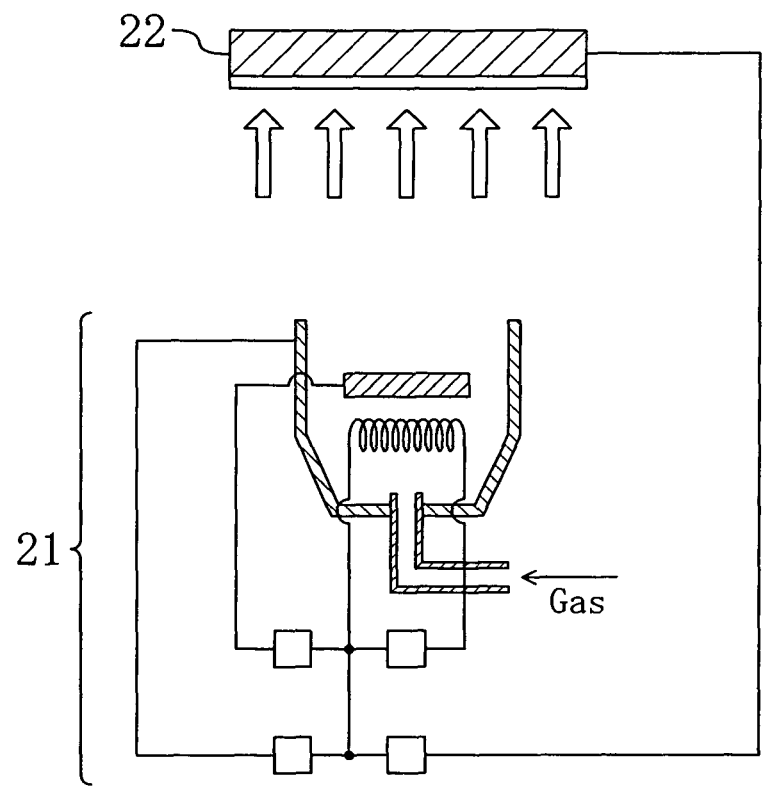
FIG. 2 is a schematic diagram of an ionization evaporation system used in a fabrication method for a stent according to an example of the invention.

FIG. 2 schematically shows an ionization evaporation system used in this example, and this is a general ionization evaporation system in which a DLC film is solidified and deposited on a target 22 by colliding, against the target 22 biased to a negative voltage, plasma generated by introducing Ar and benzene ($C_6H_6$) gases corresponding to ion sources into a DC arc discharge plasma generator 21 provided within a vacuum chamber.

A stent body 11 was set within the chamber of the ionization evaporation system of FIG. 2, and bombardment cleaning, in which Ar ions are produced by discharging after introducing an argon gas (Ar) into the chamber so as to attain a pressure of $10^{-1}$ Pa through $10^{-3}$ Pa ($10^{-3}$ Torr through $10^{-5}$ Torr) and the thus produced Ar ions are collided against the surface of the stent body, was performed for approximately 30 minutes.

Subsequently, tetramethylsilane ($Si(CH_3)_4$) was introduced into the chamber for 3 minutes, so as to form an amorphous intermediate layer with a thickness of 20 nm including silicon (Si) and carbon (C) as principal components.

After forming the intermediate layer, a $C_6H_6$ gas was introduced into the chamber, and the gas pressure was set to $10^{-1}$ Pa. $C_6H_6$ was ionized by causing discharge while continuously introducing the $C_6H_6$ into the chamber at a rate of 30 ml/min., and the ionization evaporation was performed for approximately 2 minutes, so as to form a DLC film 12 with a thickness of 30 nm on the surface of the stent body 11.

In forming the DLC film 12, a substrate voltage was set to 1.5 kV, a substrate current was set to 50 mA, a filament voltage was set to 14 V, a filament current was set to 30 A, an anode voltage was set to 50 V, an anode current was set to 0.6 A, a reflector voltage was set to 50 V and a reflector current was set to 6 mA. Also, the temperature of the stent body attained in the formation is approximately 160° C.

The intermediate layer is provided for improving the adhesiveness between the stent body 11 and the DLC film 12, and therefore, it may be omitted if sufficient adhesiveness is attained between the stent body 11 and the DLC film 12.

Although a single gas of $C_6H_6$ was used as a carbon source in this example, another hydrocarbon material or a mixed gas of a hydrocarbon material including $C_6H_6$ and a flon gas such as $CF_4$ may be used, so as to form a DLC film 12 including fluorine on the surface of the stent body 11.

Figure 3:
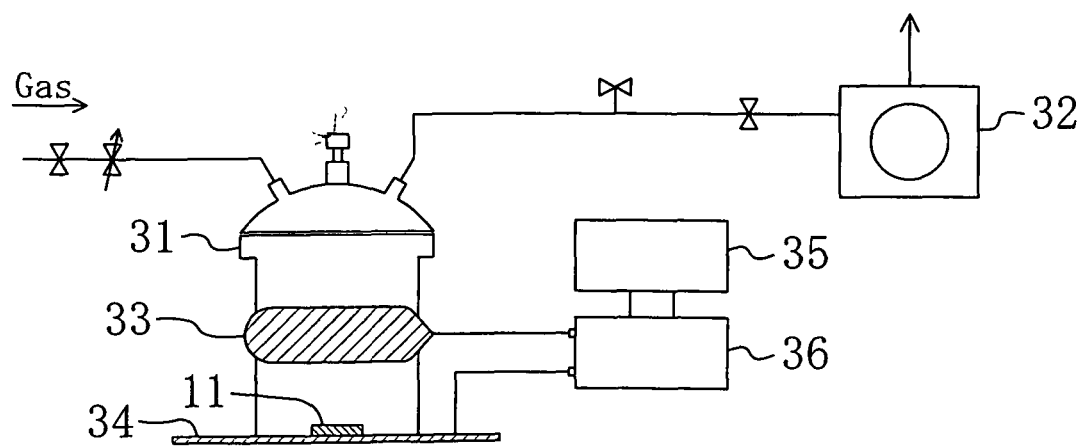
FIG. 3 is a schematic diagram of a plasma irradiation system used in the fabrication method for a stent according to the example of the invention.

Next, the DLC film 12 formed on the surface of the stent body 11 was irradiated with plasma so as to introduce functional groups into a surface portion of the DLC film 12. FIG. 3 schematically shows a plasma irradiation system used in this example.

As shown in FIG. 3, the plasma irradiation system is a general plasma irradiation system, in which an electrode 33 and an electrode 34 are provided respectively on the bottom and in the middle of a chamber 31 connected to a vacuum pump 32 and capable of exchanging gases included therein. When high-frequency waves are applied from a radio-frequency power supply 35 through a matching network 36 to the electrode 33 and the electrode 34, plasma is generated within the chamber 31.

First, the stent body 11 having the DLC film 12 was set within the chamber 31 of the plasma irradiation system, and acetylene was allowed to flow so as to attain an internal pressure of the chamber of 133 Pa. Subsequently, high-frequency waves of 50 W were applied to the electrodes 33 and 34 by using the radio-frequency power supply 35 (manufactured by Adtec Plasma Technology Co., Ltd.; AX-300; with a frequency of 13.56 MHz), so as to generate plasma within the chamber 31. The stent having the DLC film was irradiated with the plasma for approximately 30 seconds, so as to produce functional groups in a surface portion of the DLC film 12.

Alternatively, the DLC film can be activated by producing radicals in the surface portion of the DLC film by using an Ar or oxygen gas in this example.

Next, a polymer layer 13 was formed by immobilizing a polymer containing a drug 14 on the surface of the DLC film 12 into which the functional groups had been introduced. As the polymer, poly(DL-lactic acid) was used, and rapamycin was used as the drug 14. Immediately after the plasma processing, a liquid containing the polymer and the drug was sprayed all over the surface of the stent at a rate of 0.02 ml/min. for 8 minutes while rotating the stent at a rate of 120 rpm. For immobilizing the polymer, a solution prepared by mixing 1.5 wt % of poly(DL-lactic acid), 0.5 wt % of rapamycin and 98 wt % of chloroform was used. After completing the spraying, the stent was dried with nitrogen airflow for 10 minutes and further dried at room temperature under reduced pressure for twenty-four hours.

After completing the drying, the weight of the stent was measured, resulting in confirming that the amount of immobilized polymer was 0.54 mg. When the stent was observed with a stereoscopic microscope with a magnifying power of 400 times, it was found that the polymer layer 13 was uniformly coated on the surface of the stent, and no cracks and no defects such as peeling was observed. Next, the stent was mounted on a balloon catheter, and the diameter of the stent was expanded to 3.0 mm by expanding the balloon. At this point, the maximum strain of the stent was 40% at the maximum. After the expansion, the catheter was drawn off and the polymer layer 13 was observed, but no crack was found in the polymer layer 13 and no peeling of the polymer layer 13 off from the stent body 11 was observed.

In this manner, in the stent of this example, the polymer containing the drug capable of preventing arterial intimal thickening is tightly immobilized onto the surface of the stent covered with the DLC film. Therefore, even if the stent is largely deformed, the polymer layer suffers from no cracks and is never peeled off from the surface of the stent. As a result, it is possible to realize a stent in which the drug can be continuously released and a base material is minimally degraded.

Industrial Applicability

According to the stent and the method for fabricating the same of this invention, it is possible to realize a stent that is not degraded in its base material by a biogenic component and continuously releases a drug for preventing restenosis, and the invention is useful particularly as a drug release stent and a method for fabricating the same.

The invention claimed is:

1. A stent comprising:
   a tubular stent body;
   a diamond-like carbon film formed on a surface of the stent body and the surface of the diamond-like carbon film as an activated site; and
   a polymer that is immobilized on the surface of the diamond-like carbon film, contains an anti-restenosis drug and gradually releases the drug, wherein
   a surface portion of the diamond-like carbon film has a hydrophilic functional group,
   the hydrophilic functional group is bonded to a carbon atom included in the diamond-like carbon film, and
   the diamond-like carbon film has a thickness not less than 20 nm and not more than 80 nm.

2. The stent of claim 1, further comprising an intermediate layer formed between the stent body and the diamond-like carbon film,
   wherein the intermediate layer is made of an amorphous film including at least one of silicon and carbon as a principal component.

3. The stent of claim 2, wherein the intermediate layer has a thickness not less than 5 nm and not more than 100 nm.

4. The stent of claim 1,
   wherein the stent body is made of one of a metal material, a ceramic material and a polymeric material, or is a complex made of at least two of a metal material, a ceramic material and a polymeric material.

5. The stent of claim 1,
   wherein the polymer is immobilized on the surface of the diamond-like carbon film through ionic interaction.

6. The stent of claim 1, wherein the polymer is a biocompatible polymer.

7. The stent of claim 6,
   wherein the biocompatible polymer is at least one polymer or an ester of a polymer selected from the group consisting of polyurethane, polyacrylamide, polyethylene oxide, polyethylene carbonate, polyethylene, polyethylene glycol, polypropylene carbonate, polyamide, fibrin, a polymer of phospholipid, a hydrophobic/hydrophilic microphase-separated polymer, a polymer or a copolymer of hydroxyethyl methacrylate, a polymer or a copolymer of vinyl pyrrolidone, a polymer or a copolymer of a fluorine-containing monomer, a polymer or a copolymer of a Si-containing monomer, and a polymer or a copolymer of vinyl ether.

8. The stent of claim 1, wherein the polymer is a biodegradable polymer.

9. The stent of claim 8, wherein the biodegradable polymer is at least one polymer selected from the group consisting of polylactic acid, polyglycolic acid, a copolymer of polylactic acid and polyglycolic acid, collagen, gelatin, chitin, chitosan, hyaluronic acid, polyamino acid, starch, poly-ϵ-caprolactone, polyethylene succinate and poly-β-hydroxylalkanoate.

10. The stent of claim 9, wherein the biodegradable polymer includes a plasticizing agent.

11. The stent of claim 1, wherein the drug is at least one drug selected from the group consisting of an antiplatelet drug, an anticoagulant, an antifibrin, an antithrombin, an antiproliferative agent, an anticancer agent, an inhibitor of HMG-CoA reductase, alfa-interferon and genetically modified epithelial cells.

12. The stent of claim 1, wherein the activated diamond-like carbon film surface is comprised of free radicals or ion seeds.

13. The stent of claim 1, wherein the polymer is immobilized directly on the activated diamond-like carbon film surface.

14. The stent of claim 1, wherein the diamond-like carbon film substantially does not contain silicon.

* * * * *

UNITED STATES PATENT AND TRADEMARK OFFICE
CERTIFICATE OF CORRECTION

PATENT NO. : 8,435,287 B2  
APPLICATION NO. : 12/088000  
DATED : May 7, 2013  
INVENTOR(S) : Nakatani et al.

Page 1 of 1

It is certified that error appears in the above-identified patent and that said Letters Patent is hereby corrected as shown below:

ON THE TITLE PAGE:

Item [30], the Foreign Application Priority Data should read as follows:

-- Mar. 30, 2004  (JP)  ................. 2004-100186  
   Jan. 30, 2006  (JP)  ................. 2006-020926 --.

Signed and Sealed this  
Twenty-fifth Day of March, 2014

Michelle K. Lee  
*Deputy Director of the United States Patent and Trademark Office*